United States Patent [19]

Nudelman et al.

[11] 4,148,998

[45] Apr. 10, 1979

[54] PYRROLE CEPHALOSPORIN DERIVATIVES

[75] Inventors: Abraham Nudelman, Rehovot; Abraham Patchornik, Ness Ziona, both of Israel

[73] Assignee: Yeda Research and Development Co., Ltd., Rehovot, Israel

[21] Appl. No.: 839,163

[22] Filed: Oct. 4, 1977

[51] Int. Cl.$^2$ ............................................. C07D 501/36
[52] U.S. Cl. ...................................... 544/27; 424/246; 544/21
[58] Field of Search .................................. 544/27, 21

[56] References Cited

U.S. PATENT DOCUMENTS

| | | | |
|---|---|---|---|
| 3,252,973 | 5/1966 | Flynn | 544/28 |
| 3,351,596 | 11/1967 | Chamberlin | 544/16 |
| 3,459,746 | 8/1969 | Flynn | 544/28 |
| 3,516,997 | 6/1970 | Takano et al. | 544/27 |
| 3,536,698 | 10/1970 | Chauvette et al. | 544/28 |
| 3,728,342 | 4/1973 | Kjkolja | 544/28 |
| 3,799,924 | 3/1974 | Jackson | 544/28 |
| 3,833,570 | 9/1974 | Holdrege et al. | 544/27 |
| 3,985,740 | 10/1976 | Essery et al. | 544/27 |
| 4,014,874 | 3/1977 | Peter et al. | 544/27 |

*Primary Examiner*—Nicholas S. Rizzo
*Attorney, Agent, or Firm*—L. Ruth Hattan; Eugene O. Retter; George W. Rauchfuss, Jr.

[57] ABSTRACT

New pyrrole derivatives of cephalosporin compounds have been prepared which are useful as antibiotics.

17 Claims, No Drawings

PYRROLE CEPHALOSPORIN DERIVATIVES

BACKGROUND OF THE INVENTION

This invention is directed to new and useful cephalosporin derivatives and methods of preparing said derivatives.

PRIOR ART

The compounds described in the prior art may be represented by the formula

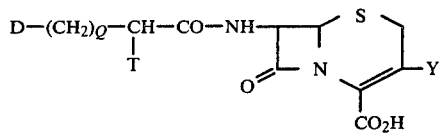

wherein D is N-pyrryl, T is hydrogen, amino, protected amino, hydroxyl, $C_{1-3}$ alkoxy, carboxyl, and $C_{1-3}$ alkanoyloxy and Q is 0 to 6 and Y is methyl, hydroxymethyl, formyl, acyloxymethyl, tertiary aminomethyl and benzoyloxymethyl. U.S. Pat. No. 3,218,318 describes and specifically claims a compound in which D is N-pyrryl, Q is zero, T is hydrogen and Y is acetyloxymethyl. U.S. Pat. No. 3,351,596 describes the compound wherein D is N-pyrryl, Q is zero, T is hydrogen and Y is hydroxymethyl which is an intermediate to the oxidized compound in which Y is a formyl group. Additional patents, such as U.S. Pat. No. 3,459,746, 3,728,342, 3,799,924, 3,252,973, and 3,536,698, E. Germany Pat. No. 109 638 and W. German Offen 2,262,477, all assigned to Eli Lilly, disclose pyrryl cephalosporin derivatives. None of these patents suggests, describes or claims the compounds of this invention.

Belgium Pat. No. 768,653 to Ciba describes compounds in which D may be N-pyrryl and Y is either a hydroxymethyl or a formyl group. This reference does not disclose the compounds of this invention.

SUMMARY OF THE INVENTION

Compounds of formula 1

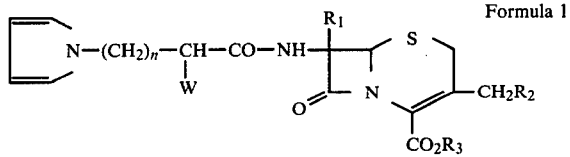

are useful as antibiotics wherein n is 0, 1, 2, or 3; W is hydrogen or a straight or branched alkyl group of 1 to 5 carbon atoms; a sulfonic acid group; a-$(CH_2)_zCO_2R_4$ group wherein z is 0 or an integer from 1 to 10 and $R_4$ is hydrogen, or non-toxic pharmaceutically acceptable cation selected from the alkali metal or alkaline earth metal groups, ammonium and an organic ammonium group, a straight or branched 1 to 4 carbon alkyl group, a straight or branched alkanoyloxymethyl group in which the alkanoyl group has from 2 to 5 carbon atoms; $R_1$ is hydrogen or methoxy; $R_2$ is hydrogen, acetyloxy, 1,3,4-thiadiazol-2-ylthio, 5-methyl-1,3,4-thiadiazol-2-ylthio, tetrazol-5-ylthio, 1-methyltetrazol-5-ylthio, 1,3,4-oxadiazol-2-ylthio, 5-methyl-1,3,4-oxadiazol-2-ylthio, 1-methyl-1,2,3-triazol-5-ylthio, 1,2,3-triazol-5-ylthio; $R_3$ is hydrogen, a non-toxic pharmaceutically acceptable cation of an alkali metal or an alkaline earth metal, ammonium or organic ammonium cations, a straight or branched alkyl group of from 1 to 4 carbon atoms, a straight or branched alkanoyloxymethyl group in which the alkanoyl moiety has from 2 to 5 carbon atoms and is straight or branched, an alkanoylaminomethyl group in which the alkanoyl moiety is straight or branched and has from 2 to 5 carbon atoms and the amine nitrogen may be substituted with a straight or branched alkyl group having 1 to 4 carbon atoms; and alkoxycarbonylaminomethyl group in which the alkoxy moiety is straight or branched and has from 1 to 4 carbon atoms and the amine nitrogen may be substituted with a straight or branched alkyl group of from 1 to 4 carbon atoms, p-(alkanoyloxy)benzyl group in which the alkanoyl moiety is straight or branched and has from 2 to 5 carbon atoms; an aminoalkanoyloxymethyl group in which the alkanoyl moiety has from 2 to 15 carbon atoms and the amino nitrogen may be mono- or di-substituted with a straight or branched alkyl group having from 1 to 4 carbon atoms; with the proviso that when n is O, W must be an alkyl group, a sulfonic acid group or a-$(CH_2)_z$-$CO_2R_4$ group with $R_4$ as defined above and $R_2$ is other than hydrogen; and with the further proviso that when n is 1, 2 or 3 and W is hydrogen, then $R_2$ must be other than acetyloxy with $R_3$ is hydrogen, and with the further proviso that when $R_3$ is other than hydrogen or a cation and W is —$(CH_2)_z$—$CO_2R_4$ with z being 1 to 10 then $R_4$ is other than hydrogen or a cation and pharmaceutically acceptable salts thereof.

DETAILED DESCRIPTION OF INVENTION

In formula 1 the substituent group as represented by $R_3$ in addition to being hydrogen or a non-toxic pharmaceutically acceptable cation may also be alkanoyloxymethyl as represented by the structure

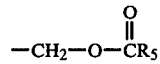

wherein $R_5$ is selected from a straight or branched alkyl group of from 1 to 4 carbon atoms; $R_3$ is an alkanoylaminomethyl or alkoxycarbonylaminomethyl as represented by the structure

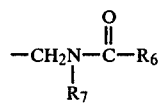

wherein $R_6$ represents a straight or branched alkyl group of from 1 to 4 carbon atoms or a straight or branched alkoxy group of from 1 to 4 carbon atoms, and $R_7$ is selected from hydrogen and a straight or branched alkyl group of from 1 to 4 carbon atoms; $R_3$ is a p-(alkanoyloxy)benzyl as represented by the structure

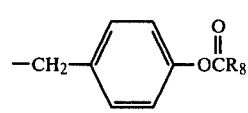

wherein $R_8$ is a straight or branched alkyl group of from 1 to 4 carbon atoms; and $R_3$ is an aminoalkanoyloxymethyl as represented by the group

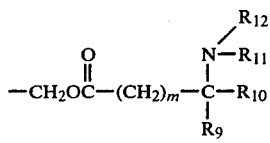

wherein m is 0 to 5, each of $R_9$ and $R_{10}$ is selected from hydrogen or a straight or branched alkyl group of from 1 to 4 carbon atoms, and each of $R_{11}$ and $R_{12}$ is selected from hydrogen or a straight or branched alkyl group of from 1 to 4 carbon atoms.

Illustrative examples of straight or branched alkyl groups of from 1 to 4 carbon atoms which $R_5$ to $R_{12}$ inclusive may represent an methyl, ethyl, n-propyl, iso-propyl, n-butyl, sec-butyl and tert-butyl. $R_6$ may represent a methoxy, an ethoxy, a propoxy or a tert-butoxy group.

In formula 1, the substituent group $R_2$ may represent in addition to hydrogen or acetyloxy or heterocyclic thio group selected from 1,3,4-thiadiazol-2-ylthio, 5-methyl-1,3,4-thiadiazol-2-ylthio, tetrazol-5-ylthio, 1-methyl-tetrazol-5-ylthio, 1,3,4-oxadiazol-2-ylthio, 5-methyl-1,3,4-oxadiazol-2-ylthio, 1,2,3-triazol-5-ylthio, or 1-methyl-1,2,3-triazol-5-ylthio, as represented by the following respective structures:

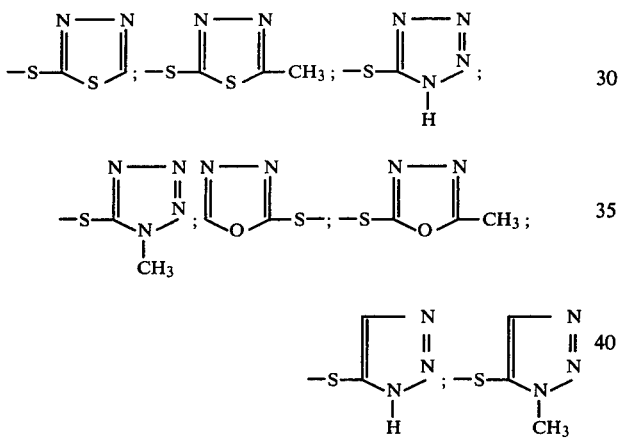

In formula 1, $R_1$ is hydrogen or methoxy. It is apparent that the group $R_1$ may be either cis or trans to the hydrogen atom at the 6-position of the cephalosporin derivative. Those compounds in which the $R_1$ group is cis to the 6-position hydrogen are preferred.

In formula 1, W may represent hydrogen, a straight or branched alkyl group of from 1 to 4 carbon atoms, a sulfonic acid group or a—$(CH_2)_z$—$CO_2R_4$ group in which Z is 0 or an integer of from 1 to 10 and $R_4$ is hydrogen, a non-toxic pharmaceutically acceptable cation selected from the alkali metal or alkaline earth metal groups, for example, sodium, potassium, calcium and magnesium ammonium or organic ammonium cations selected from a primary, secondary or tertiary amine such as cyclohexylamine, dibutylamine and pyridine; a straight or branched alkyl group of 1 to 4 carbon atoms or an alkanoyloxymethyl group in which the alkanoyl group is straight or branched and has from 2 to 5 carbon atoms. It is apparent that when W is other than hydrogen or a —$CO_2H$ group in formula 1, optical isomers result and these isomers are included within the scope of this invention.

The non-toxic pharmaceutically acceptable inorganic acid addition salts of compounds of this invention such as mineral acid addition salts, for example, hydrogen chloride, hydrogen bromide, hydrogen iodide, sulfates, sulfamate, phosphate, and organic acid addition salts, for example, maleate, acetate, citrate, oxalate, succinate, benzoate, tartrate, fumarate, malate, mandelate, and ascorbate, are also included within the scope of this invention.

Also within the scope of this invention are the non-toxic pharmaceutically acceptable salts of the compounds of formula 1 of this invention wherein W represents $(CH_2)_z$—$CO_2R_4$ ($R_4$=H), or $SO_3H$ and compounds wherein $R_3$ represents hydrogen. Illustrative non-toxic pharmaceutically acceptable salts of these acid derivatives include the alkali metal and alkaline earth metal salts such as the sodium, potassium, calcium or magnesium salts and the primary, secondary, or tertiary amine salts, for example, cyclohexylamine, diethylamine, and pyridine.

The compounds of this invention may be administered in a manner similar to that of many well-known cephalosporin compounds, for example, cephalexin, cephalothin, or cephaloglycine. They may be administered alone or in the form of pharmaceutical preparations either orally or parenterally and topically to warm blooded animals, that is, birds, and mammals, for example, cats, dogs, cows, sheep and horses, and humans. For oral administration, the compounds may be administered in the form of tablets, capsules or pills or in the form of elixirs or suspensions. For parenteral administration, they may be used in the form of a sterile aqueous solution which may contain other solutes, for example, enough saline or glucose to make the solution isotonic. For topical administration, the compounds may be incorporated in creams or ointments.

Illustrative examples of bacteria against which the compounds of this invention are active are Staphylococcus aureus, Salmonella schottmuelleri, Klebsiella pneumoniae, Diplococcus pneumoniae, and Streptococcus pyogenes.

An illustrative example of a cephalosporin derivative of this invention is 3-[(acetyloxy)methyl]-7-[[2-(4-carboethoxybutyl)-2-(1-pyrryl)acetyl]amino]-8-oxo-5-thia-1-azabicyclo[4.2.0]oct-2-ene-2-carboxylic acid.

The compounds of this invention as represented by formula 1 are prepared by coupling compounds of formula 2

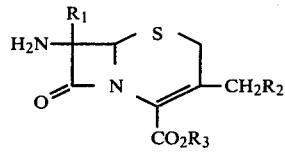

Formula 2 wherein $R_1$, $R_2$ and $R_3$ have meanings defined for formula 1 with compounds of formula 3

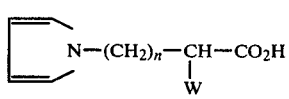

Formula 3 wherein n and W have the meanings defined for formula 1 and functional equivalents thereof.

When W is a—$(CH_2)_z$—$CO_2R_4$ group in compounds represented by formula 3 and z is from 1 to 10 then $R_4$ is other than hydrogen or a cation and when z is 0, $R_4$ is as defined in formula 1, when said compounds of formula 3 are coupled with compounds of formula 2 to give compounds represented by formula 1. Additionally, a coupling agent such as N-ethoxycarbonyl-2-ethoxy-1,2-dihydroquinoline may be used and then W is other than —$SO_3H$ and $R_3$ and $R_4$ are other than hydrogen or a cation.

Functional equivalents of the acids as represented by formula 3 include the acid halide, for example, the acid chloride, acid anhydrides, including mixed anhydrides with for example alkylphosphoric acid, lower aliphatic monoesters of carbonic acid or alkyl or aryl sulfonic acids.

The coupling reaction is generally carried out in the presence of a solvent. Suitable solvents include ethyl acetate, acetone, dioxane, acetonitrile, chloroform, ethylene chloride, tetrahydrofuran, dimethylformamide, ether, ethanol, ethanol-benzene and benzene. As hydrophilic solvents are employed, mixtures of these solvents with water are also suitable for the above reactions. The coupling reaction is generally carried out in the presence of a base, for example, triethylamine or an alkaline bicarbonate. The temperature of the reaction may vary from $-10°$ to $100°$ C., and the reaction time may vary from about ½ hour to 10 hours. The cephalosporin products are isolated by conventional methods.

Illustrative examples of coupling reactions useful in obtaining compounds of formula 1 are as follows.

The general method described by Spencer, et al., J. Med. Chem., 9, 746 (1966) is used to form formula 1 compounds. An acid of formula 3 is first converted to a functional equivalent (mixed anhydride) by reacting the acid with an alkylchloroformate in the presence of an acid acceptor (for example, triethylamine) in a solvent at about $-10°$ C. The amine with which the acid is to be coupled to form compounds as represented by formula 1 is added and the temperatures increased from about $-10°$ C. to about room temperature (about $20°$ C.). The reaction is completed and the coupled product is recovered by conventional methods. If the acid of formula 3 contains a—$(CH_2)_z$—$CO_2R_4$ group, then $R_4$ is other than hydrogen or a cation.

Another illustrative method used to prepare compounds of formula 1 involves the coupling of 1 equivalent of an acid as represented by compounds of formula 3 with 1 equivalent of an amine as represented by compounds of formula 2 in the presence of about 1 to 2 equivalents of a carbodiimide according to the general procedure described in U.S. Pat. No. 3,252,973. $R_1$, $R_2$, $R_3$, n and W are as defined for formula 1. When z has a value of from 0 to 10 then $R_4$ is other than hydrogen or a cation.

Optionally, acids as represented by compounds of formula 3 may be coupled with compounds as represented by formula 2 in the presence of N-ethoxycarbonyl-2-ethoxy-1,2-dihydroquinoline (EEDQ) provided that $R_3$ and $R_4$ are other than hydrogen or a cation. Using the general method of Belleau, et al., J. Am. Chem. Soc., 90, 1651 (1968), equivalent amounts of the acid, the amine and EEDQ are stirred in a suitable solvent for 2 to 12 hours at a temperature of about $20°$ C. to about $70°$ C. The coupled product is recovered by conventional techniques.

Illustratively, a compound as represented by formula 3 wherein W is —$(CH_2)_zCO_2R_4$ and z is 0 and $R_4$ is hydrogen is coupled to compounds as represented by formula 2 using the general procedure as described in U.S. Pat. No. 3,282,926. The monoacid chloride of a compound of formula 3 prepared as described in U.S. Pat. No. 3,282,926 is reacted with the 7-amino derivative of compounds of formula 2 in the presence of an acid acceptor at a temperature of about $0°$ C. to about $30°$ C. for from 30 minutes to 2 hours to give the coupled compound which is recovered by conventional techniques.

Illustratively, a compound of formula 3 wherein W is a —$SO_3H$ group can be coupled with a compound represented by a compound of formula 2 using the general method described in J. Med. Chem., 15, 1105 (1972). The carboxylic acid chloride of a compound of formula 3, W is —$SO_3H$, is prepared and coupled with an amine derivative of a compound of formula 2 is a suitable solvent in the presence of an acid acceptor. The compound of formula 1, W is —$SO_3H$, is recovered by conventional methods.

Compounds of formula 2 wherein $R_1$ is hydrogen, $R_3$ is hydrogen, or a cation and $R_2$ is hydrogen or acetyloxy are commercially available or may be prepared by the methods well-known in the art. The corresponding compounds wherein $R_1$ is methoxy, $R_2$ is hydrogen or acetyloxy and $R_3$ is hydrogen may be prepared by the general procedures described in U.S. Pat. No. 3,778,432.

Compounds of formula 1 and 2 wherein $R_3$ is alkanoyloxymethyl may be prepared by reacting the corresponding acid, $R_3$ is hydrogen, in the form of a salt, such as, an alkali metal salt or the triethylammonium salt with a compound of the formula:

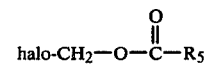

wherein halo is chlorine or bromine, and $R_5$ is a straight or branched alkyl group of from 1 to 4 carbon atoms, by the general procedure described in U.S. Pat. No. 3,655,658.

Compounds of formulas 1 and 2 wherein $R_3$ is alkanoylaminomethyl or alkoxycarbonylaminomethyl are prepared by treating the sodium salt of the corresponding acid ($R_3$=hydrogen) derivatives of formulas 1 and 2 in an organic solvent such as dimethylformamide or hexamethylphosphoramide at room temperature with an equivalent amount of an alkanoylaminomethyl halide or an alkoxycarbonylaminomethyl halide for ½ to 3 hours after which the mixture is poured into ice water. The resulting precipitated product is isolated by standard procedures.

Compounds of formulas 1 and 2 wherein $R_3$ is p-(alkanoyloxy)benzyl are prepared by adding two equivalents of the p-(alkanoyloxy)benzyl alcohol to a suspension of the sodium salt of the corresponding acid derivative, $R_3$=hydrogen, of formulas 1 and 2 and dimethylformamide or hexamethylphosphoramide after which the mixture is colled to $0°$ C. 1.2 equivalents of dicyclohexylcarbodiimide and dimethylformamide are added dropwise to the mixture with stirring. The mixture is stirred at $0°$ C. for ½ to 3 hours and then an additional 2 to 5 hours at room temperature. The formed dicyclohexylurea is removed by filtration. The filtrate is diluted with chloroform, methylene chloride or ethylacetate, washed with water, dried and evaporated to give the product.

Compounds of formulas 1 and 2 wherein $R_3$ is aminoalkanoyloxymethyl are prepared by mixing a suspension of the sodium salt of the corresponding acid, $R_3$=hydrogen, of formulas 1 and 2 and an excess of an appropriate amine protected aminoalkanoyloxymethyl halide in a solvent such as dimethylformamide, hexamethylphosphoramide or dimethylsulfoxide for 2 to 96 hours. The mixture is then diluted with a solvent such as ethylacetate or methylene chloride washed with water, aqueous base, then water. The organic phase is separated and the precipitate isolated by conventional means followed by deprotection of the amine group to give the product.

Compounds represented by formula 1 and 2 wherein $R_1$ is hydrogen or methoxy, $R_2$ is a heterocyclic thio group as described in formula 1 and $R_3$ is hydrogen are prepared by dissolving 1 equivalent of an acid, represented by compounds of formula 1 or 2 wherein $R_1$ is hydrogen or methoxy, $R_2$ is acetyloxy, and $R_3$ is hydrogen, in the form of a salt, such as the sodium salt, in about 500 to 2000 ml of water at a temperature of from about 30° to about 90° C. under a nitrogen atmosphere, and then adding 1 equivalent of a base, such as, sodium bicarbonate or triethylamine and 1 to 3 equivalents of the appropriate heterocyclic thiol selected from a compound having the following structure:

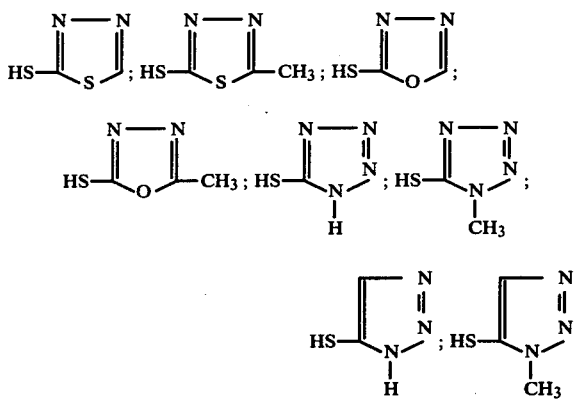

The displacement of the acetyloxy group by the heterocyclic thiol compounds is also realized when compounds of formula 1, $R_1$ is hydrogen or methoxy, $R_2$ is acetyloxy, and $R_3$ is hydrogen, are treated with an appropriate heterocyclic thiol according to the general procedure described in J. Antibiotics, 23, 131 (1966).

Compounds of formula 3 wherein W is hydrogen and n is 0, 1, 2 or 3 are prepared by the general procedure of Gloede, et al., Collect. Czech. Chem. Commun., 33, 1307 (1968). An appropriate amino acid is reacted with 2,5-dialkoxytetrahydrofuran, (the alkoxy groups are methoxy or ethoxy groups) in acetic acid at reflux temperature. The N-substituted pyrrole alkanoic acid corresponding to the amino acid is obtained. For example, when 3-aminopropanoic acid is subjected to the Gloede procedure, 3-(1-pyrryl) propanoic acid is obtained.

The method of Clemo, et. al., J. Chem. Soc. 49 (1931) may also be used. The potassium salt of pyrrole is reacted with a halogenated, usually chlorine or bromine, alkanoic ester in a hydrocarbon solvent to produce the corresponding 1-pyrryl alkanoic ester. Basic hydrolysis followed by acidification with hydrochloric acid gives the (1-pyrryl) alkanoic acid.

The compound of formula 3 when n is O and W is $CO_2H$ is prepared by the method Gloede wherein diethyl aminomalonate is reacted with 2,5-diethoxytetrahydrofuran in refluxing acetic acid. Removal of the acetic acid in vacuo and distillation of the residue gives the diethyl ester. Hydrolysis using alcoholic potassium hydroxide followed by acidification with hydrochloric acid gives the (N-pyrryl)malonic acid.

Similar procedures are used to prepare compounds of formula 3 when n is O and W is $-(CH_2)_z-CO_2R_4$, z and $R_4$ have meanings of formula 1, $-SO_3H$ and straight or branched alkyl groups of from 1 to 4 carbon atoms from the appropriately substituted amino compound.

Optionally, compounds of formula 1 wherein $R_3$ and $R_4$ are both hydrogen can be prepared by subjecting compounds of formula 1 wherein either one of or both of $R_3$ and $R_4$ is other than hydrogen or a cation to trifluoroacetic acid at 0° C. for about 10 minutes to 1 hour so as to hydrolyze a group from the carboxy group to form the free acid. The general procedure described in U.S. Pat. No. 3,657,232 is employed.

The preferred compounds of this invention are those compounds of formula 1, W is $-(CH_2)_{0-10}-CO_2R_4$, wherein $R_4$ is hydrogen or an alkyl group or a $-SO_3H$ group, $R_1$ is hydrogen, $R_2$ is acetyloxy or a heterocyclic thio group and $R_3$ is hydrogen.

The more preferred are those compounds wherein W is a $-(CH_2)_{1-10}-CO_2R_4$ with $R_4$ being hydrogen or an alkyl group, $R_1$ is hydrogen and $R_2$ is acetyloxy or a heterocyclicthio and $R_3$ is hydrogen.

EXAMPLE 1

(1-Pyrryl)malonic acid, diethylester

To a boiling solution of 32.6 g (0.4 mole) of sodium acetate in 750 ml of glacial acetic acid is added aminomalonic acid diethyl ester hydrochloride. The clear solution is refluxed for 5 minutes, then 25.1 g (about 0.2 mole) of 2.5-diethoxytetrahydrofuran (90–95% pure) is added in one portion and the mixture boiled an additional two minutes. The acetic acid is flash evaporated and the residue is distilled. Diethyl 1-pyrrylmalonate is obtained in 64% yield, b.p. 143°–146° C./0.1 mm Hg. The NMR spectrum indicates a small amount of impurity. 14.3 g of the distilled ester is chromatographed on 220 g of silica gel, eluted with 3/2 ether/hexane to give 12.9 g of pure diethyl 1-pyrrylmalonate as shown by a single spot on the thin layer chromatograph plate.

NMR (CDCl$_3$) ppm ($\delta$) 1.22 (t,6), 4.24 (q,4) 5.42 (s,1), 6.18 (t,2), 6.80 (t,2)

EXAMPLE 2

Monoethyl ester of (1-pyrryl)malonate

To a solution of diethyl (1-pyrryl)malonate (4.5 g, 0.02 mole) in 25 ml of absolute ethanol is added 25 ml (0.02 mole) of 0.8 N ethanolic potassium hydroxide. This solution is stirred overnight. The solvent is flash evaporated and the residue is dissolved in 25 ml of water and washed twice with 50 ml of ether. The aqueous phase is separated, acidified to pH of 2.5, saturated with sodium chloride and extracted twice with 80 ml of ether. The ether extracts are combined, dried and evaporated to give 2.3 g (58% yield) of the monoethylester as an oil.

NMR (CDCl$_3$) ppm ($\delta$) 1.22 (t,3), 4.3 (q,2) 5.45 (s,1); 6.22 (t,2), 6.8 (t,2)

A small amount of ethyl 1-pyrrylacetate is present as a contaminant.

EXAMPLE 3

(1-Pyrryl)malonic Acid

A solution of 4.5 g (0.02 mole) of diethyl (1-pyrryl)-malonate in 25 ml of absolute ethanol is mixed with 50 ml of 0.8 N alcoholic potassium hydroxide (0.04 mole) and stirred overnight at room temperature. The solution is evaporated to dryness and the NMR[($D_2O$) ppm ($\delta$) 5.3 (s,1) 6.48 (t,2), 7.0 (t,2)] of the residue indicates the desired dipostassium salt was obtained.

The residue is dissolved in a small amount of water and acidified to pH of 2 with 6 N hydrochloric acid. The aqueous phase is extracted with ether. The ether extracts are combined, dried and evaporated to give 1.6 g (47%) of (1-pyrryl)malonic acid as an oil.

NMR (DMSO-$D_6$) ppm ($\delta$) 5.41 (s,1), 6.02 (t,2), 6.72 (t,2)

EXAMPLE 4

2-(1-Pyrryl)pentanoic acid

Pentanoic acid (0.1 mole) is added to about 50 ml of thionyl chloride and the mixture is refluxed for about 5 minutes. Then bromine (0.105 mole) is added at reflux temperatures and the bromine is rapidly consumed. The excess thionyl chloride is removed under vacuo and the residue is cautiously poured into an excess of ethyl alcohol. Removal of the ethyl alcohol gives ethyl-2-bromopentanoate.

To a solution of potassium phthalimide (0.1 mole) in about 50 ml of dimethylformamide (DMF) is added 1 equivalent of ethyl-2-bromopentanoate. The temperature is maintained at about 60° C. for 10 minutes. Chloroform is added to the cooled DMF solution and the mixture is poured into water. The phases are separated and the aqueous phase is extracted with chloroform. The chloroform extracts are combined, extracted with 0.1 N sodium hydroxide and with water. After drying over sodium sulfate, the chloroform is removed to give ethyl α-phthalimidopentanoate.

A mixture of ethyl α-phthalimidopentanoate (0.01 mole), methanol and 85% aqueous hydrazine hydrate (0.02 mole) is refluxed for about 1 hour. On cooling, water is added to the mixture and the methanol removed. Concentrated hydrochloric acid is added and the mixture is heated at reflux for 1 hour. On cooling the solid, phthalhydrazide is removed by filtration. The solution is concentrated to remove the hydrochloric acid, water is added, and the aqueous solution is neutralized with sodium hydroxide. Cooling to 0° C. overnight gives 2-aminopentanoic acid.

2-Aminopentanoic acid (0.2 mole) is added to a solution of sodium acetate (0.2 mole) in about 300 ml of glacial acetic acid. This solution is heated to effect solution and is then refluxed for 5 minutes. To the refluxing solution is added (0.2 mole) 2.5-dimethoxytetrahydrofuran as quickly as possible. The mixture is refluxed for a further 2 minutes and the acetic acid is flash evaporated. The residue is taken up in ethyl acetate, washed with water, dried and the solvent removed under vacuo to give 2-(1-pyrryl)pentanoic acid.

In like manner employing the steps above and using the appropriate amounts of propanoic acid and butanoic acid in place of pentanoic acid gives respectively:
2-(1-pyrryl)propanoic acid, and
2-(1-pyrryl)butanoic acid.

EXAMPLE 5

2-Bromohexanedioic acid, 6-ethyl ester

Using a modification of the procedure of Schwenk and Papa, J. Am. Chem. Soc., 70 3626 (1948), 2-bromohexanedioic acid, 6-ethyl ester is prepared. The monoethyl ester of hexanedioic acid (0.05 mole) is added to an excess of thionyl chloride (50 ml) and the mixture is refluxed. Then a slight excess of bromine (0.06 mole) is added to the refluxing mixture. The bromine reacts quite rapidly as evidenced by the disappearance of the brown color. Removal of the thionyl chloride under vacuo yields the 2-bromohexanedioic acid, 6-ethyl ester which is used without further purification.

In like manner and using sufficient quantities of reactants such as the monoethyl esters of the following dicarboxylic acids: butanedioic acid, pentanedioic acid, heptanedioic acid, octanedioic acid, nonanedioic acid, decanedioic acid, undecanedioic acid and dodecanedioic acid in place of the monoethyl ester of hexanedioic acid, gives respectively:
2-bromobutanedioic acid, 4-ethyl ester,
2-bromopentanedioic acid, 5-ethyl ester,
2-bromoheptanedioic acid, 7-ethyl ester,
2-bromooctanedioic acid, 8-ethyl ester,
2-bromononanedioic acid, 9-ethyl ester,
2-bromodecanedioic acid, 10-ethyl ester,
2-bromoundecanedioic acid, 11-ethyl ester, and
2-bromododecanedioic acid, 12-ethyl ester.

EXAMPLE 6

2-(1-Pyrryl)hexanedioic acid, 6-ethyl ester

Potassium pyrrole (2 equivalents) prepared according to the method of Clemo and Romage, J. Chem. Soc., (1931), 49, is slurried in benzene to form a suspension. This suspension is slowly added to 1 equivalent of 2-bromohexanedioic acid, 6-ethyl ester which is dissolved in benzene. After the exothermic reaction subsided, the reaction mixture is heated at water bath temperature for about one hour. The mixture is cooled to room temperature and cautiously added to water. The aqueous mixture is acidified to pH of 6 with hydrochloric acid and then extracted with ether. The ether fraction is dried, the solvents (ether and benzene) are removed to give 2-(1-pyrryl)hexanedioic acid, 6-ethyl ester.

In like manner and using the proper quantities of 2-bromobutanedioic acid, 4-ethyl ester, 2-bromopentanedioic acid, 5-ethyl ester; 2-bromoheptanedioic acid, 7-ethyl ester; 2-bromooctanedioic acid, 8-ethyl ester; 2-bromononanedioic acid, 9-ethyl ester; 2-bromodecanedioic acid, 10-ethyl ester; 2-bromoundecanedioic acid, 11-ethyl ester; and 2-bromododecanedioic acid, 12-ethyl ester in place of 2-bromohexanedioic acid, 6-ethyl ester gives the following pyrrole derivatives:
2-(1-pyrryl)butanedioic acid, 4-ethyl ester,
2-(1-pyrryl)pentanedioic acid, 5-ethyl ester,
2-(1-pyrryl)heptanedioic acid, 7-ethyl ester,
2-(1-pyrryl)octanedioic acid, 8-ethyl ester,
2-(1-pyrryl)nonanedioic acid, 9-ethyl ester,
2-(1-pyrryl)decanedioic acid, 10-ethyl ester,
2-(1-pyrryl)undecanedioic acid, 11-ethyl ester, and
2-(1-pyrryl)dodecanedioic acid, 12-ethyl ester.

EXAMPLE 7

4-(1-Pyrryl)butanoic acid

Ethyl 4-bromobutanoate is converted to the corresponding 4-amino-compound by means of the Gabriel Amine synthesis. See Angew Chem. Int. Ed., 7, 919 (1968).

Ethyl 4-aminobutanoate hydrochloride (0.2 mole) is added to 300 ml glacial acetic acid containing (0.3 mole) sodium acetate. The mixture is heated until the solution becomes clear and then 2,5-dimethoxy tetrahydrofuran (about 0.2 mole) is added as quickly as possible. The solution is refluxed for an additional two minutes and the acetic acid is flash evaporated. The residue is distilled to give ethyl 4-(1-pyrryl)butanoate. The acid is obtained by hydrolyzing the ester in alcoholic sodium hydroxide followed by neutralization with hydrochloric acid.

In like manner and using the proper amounts of reactants ethyl 3-bromopanoate and ethyl-2-chloroacetate in place of ethyl 4-bromobutanoate gives the following compounds respectively:

3-(1-pyrryl)propanoic acid, and 2-(1-pyrryl)acetic acid.

EXAMPLE 8

α-Sulfo-α-aminoacetic acid

The diacid chloride of α-sulfo-α-chloroacetic acid is prepared according to the procedure of LeBerre, Bull. Soc. Chem. Fr. 1973, (1) (Pt.2) 210–14. The diacid chloride is cautiously poured into ethanol (100%) to form the diethyl ester. Removal in vacuo of the ethanol gives the diethylester of α-sulfo-α-chloroacetic acid.

To a solution of 50 ml dimethylformamide (DMF) containing 0.1 mole of potassium phthalimide is added an equivalent amount of the diethyl ester of α-sulfo-α-chloroacetic acid. The temperature of the reaction mixture increases due to the exothermic nature of the reaction. The mixture is stirred for about 1 hour after which chloroform is added. The DMF-chloroform solution is added to water, thorougly stirred and the phases are separated. The aqueous phase is extracted with chloroform. All of the chloroform extracts are combined, dried, and the chloroform is flash evaporated to give diethyl α-sulfo-α-phthalimidoacetate.

A mixture of 0.01 mole of diethyl α-sulfo-α-phthalimidoacetate, 50 ml of methanol and 0.02 mole of hydrazine hydrate is heated at reflux for 1 hour. The mixture is cooled, water is added and the methanol is removed in vacuo. 12 N hydrochloric acid is added and the mixture is heated under reflux for 1 hour. On cooling to 0° C., phthalhydrazide precipitates and is removed by filtration. The filtrate is evaporated to give a residue which is taken up in 0.5 N hydrochloric acid. Cooling to 0° C. overnight gives α-sulfo-α-aminoacetic acid hydrochloride.

EXAMPLE 9

α-Sulfo-α-(1-pyrryl)acetic acid

To a solution of sodium acetate (0.1 mole) in about 300 ml of glacial acetic acid is added about 0.05 mole of α-sulfo-α-aminoacetic acid hydrochloride. The solution is heated to reflux for 5 minutes, 2,5-dimethoxytetrahydrofuran (1 equivalent based on α-sulfo-α-aminoacetic acid hydrochloride) is added as quickly as possible, and the solution refluxed for an additional 2 minutes. The acetic acid is flash evaporated leaving a residue which is taken up in ethylacetate. The ethyl acetate is filtered, dried and evaporated to give α-sulfo-α-(1-pyrryl) acetic acid.

EXAMPLE 10

3-[(Acetyloxy)methyl]-7[[2-carboethoxy-2-(1-pyrryl)-acetyl]amino]-8-oxo-5-thia-1-azabicyclo[4.2.0]oct-2-ene-2-carboxylic acid A solution of the monoethyl ester of 2(1-pyrryl) propanedioic acid (1 g., 5.07 mM) and 0.87 g. (5.2 mM) of N, N''-carbonyldiimidazole in 10 ml of dimethylformamide is stirred at room temperature for one hour. In a second flask, 3[(acetyloxy)methyl]-7-amino-8-oxo-5-thia-1-azabicyclo[4.2.0]oct-2-ene-2-carboxylic acid (1.37 g, 5.07 mM) is dissolved in 35 ml of chloroform upon the addition of 2.05 g (20.3 mM) of triethylamine and is stirred under nitrogen for 30 minutes in the presence of Linde 44 molecular sieves. The two solutions are combined and the mixture stirred for 4 hours after the addition of 0.5 g of charcoal. The reaction mixture is filtered, concentrated by flash evaporation and the residue is dissolved in 25 ml of water and washed several times with ether. The aqueous phase is covered with 50 ml of ethyl acetate and is then acidified to pH of 2.5 with 6 N hydrochloric acid. A small amount of solid is removed by filtration and the organic phase is separated, dried and concentrated to 5 ml. The title compound is obtained as a powder (425 mg., 19% yield) upon addition of the ethyl acetate solution to hexane. NMR (DMSO-$D_6$-$D_2O$) ppm ($\delta$) 1.30 (t,3), 2.08 (s,3), 3.5 (broad s,2), 4.31 (q,2), 5.0 (m,3), 5.55 (s,1), 5.8 (m,1), 6.22 (m,2), 6.9 (m,2).

In like manner and using the proper quantities of reactants, 2-(1-pyrryl)butanedioic acid, 4-ethyl ester; 2-(1-pyrryl)pentanedioic acid, 5-ethyl ester; 2-(1-pyrryl)-hexanedioic acid, 6-ethyl ester; 2-(1-pyrryl)heptanedioic acid, 7-ethyl ester; 2-(1-pyrryl)octanedioic acid, 8-ethyl ester; 2-(1-pyrryl)nononedioic acid, 9-ethyl ester; 2-(1-pyrryl)decanedioic acid, 10-ethyl ester; 2-(1-pyrryl)-undecanedioic acid, 11-ethyl ester; 2-(1-pyrryl)-dodecanedioic acid, 12-ethyl ester in place of 2-(1-pyrryl)propanedioic acid, ethyl ester gives the following cephalosporin derivatives respectively:

3-[(Acetyloxy)methyl]-7-[[2-(carboethoxymethyl)-2-(1-pyrryl)acetyl]amino]-8-oxo-5-thia-1-azabicyclo[4.2.0]oct-2-ene-2-carboxylic acid, 3-[(Acetyloxy)methyl]-7-[[2-(2-carboethoxyethyl)-2-(1-pyrryl)acetyl]amino]-8-oxo-5-thia-1-azabicyclo[4.2.0]-oct-2-ene-2-carboxylic acid, 3-[(Acetyloxy)methyl]-7-[[2-(3-carboethoxypropyl)-2-(1-pyrryl)acetyl]amino]-8-oxo-5-thia-1-azabicyclo[4.2.0]oct-2-ene-2-carboxylic acid, 3-[(Acetyloxy)methyl]-7-[[2-(4-carboethoxybutyl)-2-(1-pyrryl)acetyl]amino]-8-oxo-5-thia-1-azabicyclo[4.2.0]oct-2-ene-2-carboxylic acid, 3-[(Acetyloxy)methyl]-7-[[2-(5-carboethoxypentyl)-2-(1-pyrryl)acetyl]amino]-8-oxo-5-thia-1-azabicyclo[4.2.0]oct-2-ene-2-carboxylic acid, 3-[(Acetyloxy)methyl]-7-[[2-(6-carboethoxyhexyl)-2-(1-pyrryl)acetyl]amino]-8-oxo-5-thia-1-azabicyclo[4.2.0]oct-2-ene-2-carboxylic acid, 3-[(Acetyloxy)methyl]-7-[[2-(7-carboethoxyheptyl)-2-(1-pyrryl)acetyl]amino]-8-oxo-5-thia-1-azabicyclo[4.2.0]-oct-2-ene-2-carboxylic acid, 3-[(Acetyloxy)methyl]-7-[[2-(8-carboethoxyoctyl)-2-(1-pyrryl)acetyl]amino]-8-oxo-5-thia-1-azabicyclo[4.2.0]oct-2-ene-2-carboxylic acid, and 3-[(Acetyloxy)methyl]-7-[[2-(9-carboethoxynonyl)-2-(1-pyrryl)acetyl]amino]-8-oxo-5-thia-1-azabicyclo[4.2.0]-oct-2-ene-2-carboxylic acid.

EXAMPLE 11

3-(Acetyloxy)methyl-7-[[4-(1-pyrryl)butyryl]amino]-8-oxo-5-thia-1-azabicyclo[4.2.0]-oct-2-ene-2-carboxylic acid 4-(1-Pyrryl)butanoic acid (0.05 mole) is dissolved in 50 ml of tetrahydrofuran (THF) and 0.05 mole of triethylamine is added. This mixture is cooled to −10° C. and 0.05 mole of isobutylchloroformate is added. The mixture is stirred for 0.5 hours at −5° C. and then 0.05 mole of 3-[(acetyloxy)methyl]-7-amino-8-oxo-5-thia-1-azabicyclo[4.2.0]oct-2-ene-2-carboxylic acid and 0.075 mole of triethyl amine in 50 ml of THF (precooled) is added. The mixture is stirred at 0° C. for 1 hour and then warmed to room temperature. The mixture is diluted with water and extracted with ethyl acetate. The aqueous layer is acidified and extracted with ethyl acetate. The ethyl acetate extracts are combined, dried, filtered, and the solvent evaporated to give the title compound.

In like manner and using the proper amounts of 3-(1-pyrryl)propanoic acid and 2-(1-pyrryl)acetic acid in place of 4-(1-pyrryl)butanoic acid gives respectively: 3-[(Acetyloxy)methyl]-7-[[3-(1-pyrryl)propionyl]amino]-8-oxo-5-thia-1-azabicyclo[4.2.0]oct-2-ene-2-carboxylic acid and 3-[(acetyloxy)methyl]-7-[[2-(1-pyrryl)acetyl]-amino]-8-oxo-5-thia-1-azabicyclo[4.2.0]oct-2-ene-2-carboxylic acid.

EXAMPLE 12

7-[[4-(1-Pyrryl)butyryl]amino]-3-[[(1-methyltetrazol-5-yl)thio]methyl]-8-oxo-5-thia-1-azabicyclo[4.2.0]oct-2-ene-2-carboxylic acid, tert-butyl ester 3-[(Acetyloxy)methyl]-7-amino-8-oxo-5-thia-1-azabicyclo[4.2.0]oct-2-ene-2-carboxylic acid, tert-butyl ester is prepared according to the procedure in J. Med. Chem., 9, 444 (1966). The acetyloxy group in the 3 position is displaced by 1-methyltetrazol-5-ylthiol in basic medium using the general method described in J. Antibiotics, 23, 131, (1970).

7-Amino-3-[[(1-methyltetrazol-5-yl)thio]methyl-8-oxo-5-thia-1-azabicyclo[4.2.0]oct-2-ene-2-carboxylic acid, tert-butyl ester (5 mM), 4-(1-pyrryl)butanoic acid (5 mM), and N-ethoxycarbonyl-2-ethoxy-1,2-dihydroquinoline (5 mM) were dissolved in 100 ml of ethyl acetate. The mixture was stirred for 3 to 4 hours at room temperature and then extracted with aqueous sodium bicarbonate, 1.0N hydrochloric acid and saturated sodium chloride. The ethyl acetate was dried over magnesium sulfate, filtered and evaporated to give the title compound.

In like manner using the appropriate quantities of reagents such as 2-(1-pyrryl)pentanoic acid and 2-(1-pyrryl)propanoic acid in place of 4-(1-pyrryl)butanoic acid gives the following cephalosporin derivatives respectively:

7-[[2-(1-pyrryl)-2-propylacetyl]amino]-3-[[(1-methyltetrazol-5-yl)thio]methyl]-8-oxo-5-thia-1-azabicyclo[4.2.0]oct-2-ene-2-carboxylic acid, tert-butyl ester; and 7-[[2-(1-pyrryl)methylacetyl]amino]-3-[[(1-methyltetrazol-5-yl)thio]methyl]-8-oxo-5-thia-1-azabicyclo[4.2.0]-oct-2-ene-2-carboxylic acid, tert-butyl ester.

EXAMPLE 13

3-[(Acetyloxy)methyl]-7-[[2-sulfo-2-(1-pyrryl)acetyl]-amino]-8-oxo-5-thia-1-azabicyclo[4.2.0]oct-2-ene-2-carboxylic acid 2-Sulfo-2-(1-pyrryl)acetic acid is treated with thionyl chloride in ether at room temperature according to the general procedure in J. Med. Chem., 15, 1105 (1972) until the evolution of gas stops. Dimethylformamide is added, the solution is warmed to about 40° C. for 1 hour. Then ether is added, followed by hexane and the solution cooled to about −25° C. 2-Sulfo-2-(1-pyrryl)acetyl chloride is isolated from the solvent by decantation.

A solution of 2-sulfo-2-(1-pyrryl)acetyl chloride (1 equivalent) in ether is added to 3-[(acetyloxy)methyl]-7-amino-8-oxo-5-thia-1-azabicyclo[4.2.0]-oct-2-ene-2-carboxylic acid (1 equivalent) and sodium bicarbonate (about 3 equivalents) in water at about 0° C. After about 30 minutes the phases are separated, the pH adjusted to about 6.5 and the aqueous phase extracted with ethyl acetate. The ethyl acetate is dried over megnesium sulfate, filtered and evaporated to give the title compound.

EXAMPLE 14

7-[[2-Carboethoxy-2-(1-pyrryl)acetyl]amino]-3-[[(1-methyltetrazol-5-yl)thio]methyl]-8-oxo-5-thia-1-azabicyclo[4.2.0]oct-2-ene-2-carboxylic acid 3-[(Acetyloxy)methyl]-7-[[2-carboethoxy-2-(1-pyrryl)acetyl]amino]-8-oxo-5-thia-1-azabicyclo[4.2.0]-oct-2-ene-2-carboxylic acid, 1 equivalent, is added to an aqueous buffer solution at a pH of between 6.5–7.0. Then 1 equivalent of 1-methyltetrazol-5-ylthiol and about 1 equivalent of sodium bicarbonate is added. This mixture is heated for about 5 hours at 60° C. At the end of the heating period, the pH of the mixture is adjusted to about 2.0 with 6N HCl. The acidified mixture is extracted with ethyl acetate which is then washed with water, saturated sodium chloride solution and finally dried over magnesium sulfate. Flash evaporation of the ethyl acetate gives the title compound.

In like manner and using the appropriate quantities of reagents, 3-[(acetyloxy)methyl]-7-[[2-(carboethoxymethyl)-2-(1-pyrryl)acetyl]amino]-8-oxo-5-thia-1-azabicyclo[4.2.0]oct-2-ene-2-carboxylic acid;

3-[(Acetyloxy)methyl]-7-[[2-(4-carboethoxybutyl)-2-(1-pyrryl)acetyl]amino]-8-oxo-5-thia-1-azabicyclo[4.2.0]oct-2-ene-2-carboxylic acid; and 3-[(Acetyloxy)methyl]-7-[[2-(8-carboethoxyoctyl)-2-(1-pyrryl)acetyl]amino]-8-oxo-5-thia-1-azabicyclo[4.2.0]oct-2-ene-2-carboxylic acid in place of 3-[(acetyloxy)methyl]-7-[[2-carboethoxy-2-(1-pyrryl)acetyl]amino]-8-oxo-5-thia-1-azabicyclo[4.2.0]oct-2-ene-2-carboxylic acid gives the following respective compounds:

7-[[2-(carboethoxymethyl)-2-(1-pyrryl)acetyl]amino]-3-[[1-methyltetrazol-5-yl)thio]methyl]-8-oxo-5-thia-1-azabicyclo[4.2.0]oct-2-ene-2-carboxylic acid;

7-[[2-(4-carboethoxybutyl)-2-(1-pyrryl)acetyl]amino]-3-[[(1-methyltetrazol-5-yl)thio]methyl]-8-oxo-5-thia-1-azabicyclo[4.2.0]oct-2-ene-2-carboxylic acid; and 7-[[2-(8-carboethoxyoctyl)-2-(1-pyrryl)acetyl]amino]-3-[[(1-methyltetrazol-5-yl)thio]methyl]-8- oxo-5-thia-1-azabicyclo[4.2.0]oct-2-ene-2-carboxylic acid.

EXAMPLE 15

7-[[2-Carboethoxy-2-(1-pyrryl)acetyl]amino]-3-[[(tetrazol-5-yl)thio]methyl]-8-oxo-5-thia-1-azabicyclo[4.2.0]oct-2-ene-2-carboxylic acid 2-(1-Pyrryl)propanedioic acid, 3-ethyl ester, 1 equivalent and 1 equivalent of triethylamine is added to tetrahydrofuran (THF) which is cooled to 0° C. While stirring, iso-butyl chloroformate, 1 equivalent, is added and the temperature is maintained at 0° C. for about 15 minutes. A cold solution of 7-amino-3-[[(tetrazol-5-yl)thio]methyl]-8-oxo-5-thia-1-azabicyclo[4.2.0]oct-2-ene-2-carboxylic acid, 1equivalent, and triethylamine, 1 equivalent, in 50% aqueous THF is added with stirring to the previous solution.

The mixture is stirred at 5° for 1 hour and at room temperature for an additional hour. The tetrahydrofuran is evaporated and the residue is dissolved in water and is washed with ethyl acetate. The aqueous phase is covered with a fresh layer of ethyl acetate, cooled in ice and acidified to pH of 3 with 6N hydrochloric acid. The mixture is filtered and the ethyl acetate separated. The aqueous phase is washed with fresh ethyl acetate. The combined ethyl acetate washings are dried over magnesium sulfate, treated with charcoal, filtered and concentrated. The concentrate is added to a stirred mixture of ether-hexane which precipitates the title compound which is recovered by filtration.

In like manner and using the appropriate quantities of reactants, substitution of 7-amino-3-[[(1,3,4-thiadiazol-2-yl)thio]methyl]-8-oxo-5-thia-1-azabicyclo[4.2.0]oct-2-ene-2-carboxylic acid, and
7-amino-3-[[(5-methyl-1,3,4-thiadiazol-2-yl)thio]methyl]-8-oxo-5-thia-1-azabicyclo[4.2.0]oct-2-ene-2-carboxylic acid for 7-amino-3-[[(tetrazol-5-yl)thio]methyl]-8-oxo-5-thia-1-azabicyclo[4.2.0]oct-2-ene-2-carboxylic acid for 7-amino-3-[[(tetrazol-5-yl)thio]methyl-8-oxo-5-thia-1-azabicyclo[4.2.0]oct-2-ene-2-carboxylic acid gives the following derivatives:

7-[[2-carboethoxy-2-(1-pyrryl)acetyl]amino]-3-[[1,3,4-thiadiazol-2-yl)thio]methyl]-8-oxo-5-thia-1-azabicyclo[4.2.0]oct-2-ene-2-carboxylic acid, and
7-[[2-carboethoxy-2-(1-pyrryl)acetyl]amino]-3-[[5-methyl-1,3,4-thiadiazol-2-yl)thio]methyl)-8-oxo-5-thia-1-azabicyclo[4.2.0]oct-2-ene-2-carboxylic acid.

EXAMPLE 16

3-[(Acetyloxy)methyl]-7-[[2-carboxy-2-(1-pyrryl)acetyl]amino]-8-oxo-5-thia-1-azabicyclo[4.2.0]oct-2-ene-2-carboxylic acid 3-[(Acetyloxy)methyl]-7-[[2-carboethoxy-2-(1-pyrryl)acetyl]amino]-8-oxo-5-thia-1-azabicyclo[4.2.0]-oct-2-ene-2-carboxylic acid is added to trifluoroacetic acid (TFA) maintained at 0° C. This mixture is stirred for about 30 minutes, warmed to about 20° C. for about 30 minutes and then warmed (maximum of 25° C.) under vacuum to remove the TFA. The acid is taken up in ethyl acetate. The ethyl acetate is washed with water, dried over magnesium sulfate, filtered and partially concentrated. The title compound was recovered from the solvent by filtration.

In like manner substituting

3-[(Acetyloxy)methyl]-7-[[2-(3-carboethoxypropyl)-2-(1-pyrryl)acetyl]amino]-8-oxo-5-thia-1-azabicyclo[4.2.0]oct-2-ene-2-carboxylic acid,
3-[(Acetyloxy)methyl]-7-[[2-(6-carboethoxyhexyl)-2-(1-pyrryl)acetyl]amino]-8-oxo-5-thia-1-azabicyclo[4.2.0]oct-2-ene-2-carboxylic acid,
3-[(Acetyloxy)methyl]-7-[[2-(9-carboethoxynonyl)-2-(1-pyrryl)acetyl]amino]-8-oxo-5-thia-1-azabicyclo[4.2.0]oct-2-ene-2-carboxylic acid,
7-[[2-carboethoxy-2-(1-pyrryl)acetyl]amino]-3-[[(1,3,4-thiadiazol-2-yl)thio]methyl]-8-oxo-5-thia-1-azabicyclo-[4.2.0]oct-2-ene-2-carboxylic acid,
7-[[2-carboethoxy-2-(1-pyrryl)acetyl]amino]-3-[[(tetrazol-5-yl)thio]methyl]-8-oxo-5-thia-1-azabicyclo[4.2.0]oct-2-ene-2-carboxylic acid, and
7-[[2-carboethoxy-2-(1-pyrryl)acetyl]amino]-3-[[(1-methyltetrazol-5-yl)thio]methyl]-8-oxo-5-thia-1-azabicyclo[4.2.0]oct-2-ene-2-carboxylic acid, for 3-[(acetyloxy)methyl]-7-[[2-carboethoxy-2-(1-pyrryl)acetyl]-amino]-8-oxo-5-thia-1-azabicyclo[4.2.0]oct-2-ene-2-carboxylic acid gives the respective acids:

3-[(Acetyloxy)methyl]-7-[[2-(3-carboxypropyl)-2-(1-pyrryl)acetyl]amino]-8-oxo-5-thia-1-azabicyclo[4.2.0]-oct-2-ene-2-carboxylic acid,
3-[(Acetyloxy)methyl]-7-[[2-(6-carboxyhexyl)-2-(1-pyrryl)acetyl]amino]-8-oxo-5-thia-1-azabicyclo[4.2.0]-oct-2-ene-2-carboxylic acid,
3-[(Acetyloxy)methyl]-7-[[2-(9-carboxynonyl)-2-(1-pyrryl)acetyl]amino]-8-oxo-5-thia-1-azabicyclo[4.2.0]-oct-2-ene-2-carboxylic acid,
7-[[2-carboxy-2-(1-pyrryl)acetyl]amino]-3-[[(1,3,4-thiadiazol-2-yl)thio]methyl]-8-oxo-5-thia-1-azabicyclo-[4.2.0]oct-2-ene-2-carboxylic acid,
7-[[2-carboxy-2-(1-pyrryl)acetyl]amino]-3-[[(tetrazol-5-yl)thio]methyl]-8-oxo-5-thia-1-azabicyclo[4.2.0]oct-2-ene-2-carboxylic acid, and
7-[[2-carboxy-2-(1-pyrryl)acetyl]amino]-3-[[(1-methyl-tetrazol-5-yl)thio]methyl]-8-oxo-5-thia-1-azabicyclo-[4.2.0]oct-2-ene-2-carboxylic acid.

EXAMPLE 17

3-[(Acetyloxy)methyl]-7-[[2-carboethoxy-2-(1-pyrryl)-acetyl]amino]-8-oxo-5-thia-1-azabicyclo[4.2.0]oct-2-ene-2-carboxylic acid, 2-amino-3-methyl butylryloxymethyl ester A suspension of 5 grams of 3-[(acetyloxy)methyl]-7-[[2-carboethoxy-2-(1-pyrryl)acetyl]amino]-8-oxo-5-thia-1-azabicyclo[4.2.0]oct-2-ene-2-carboxylic acid sodium salt and 8.5 grams of N-tert-butoxycarbonyl-L-valine chloromethyl ester, prepared by the general procedure described in W. German Offen. No. 2,236,620 are mixed in 100 ml of dimethylformamide (DMF) and stirred for 72 hours. The mixture is diluted with ethyl acetate, washed with water, aqueous sodium bicarbonate and again with water. The ethyl acetate portion is dried over magnesium sulfate, filtered and evaporated to dryness to give 3-[(acetyloxy)methyl]-7-[[2-carboethoxy-2-(1-pyrryl)acetyl]-amino]-8-oxo-5-thia-1-azabicyclo[4.2.0]oct-2-ene-2-carboxylic acid N-tert-butoxycarbonyl-2-amino-3-methylbutyryloxymethyl ester from which the protecting group can be removed by standard procedures to give the title compound.

EXAMPLE 18

3-[(Acetyloxy)methyl]-7-[[2-carboethoxy-2-(1-pyrryl)acetyl]amino]-8-oxo-5-thia-1-azabicyclo[4.2.0]oct-2-ene-2-carboxylic acid pivaloyloxymethyl ester The sodium salt of 3-[(acetyloxy)methyl]-7-[[2-carboethoxy-2-(1-pyrryl)acetyl]amino]-8-oxo-5-thia-1-azabicyclo[4.2.0]oct-2-ene-2-carboxylic acid (3 grams) was added to about 40 ml of dry dimethylformamide (DMF) and stirred for about 30 minutes. Then 4.0 ml of chloromethyl pivalate in 5 ml of DMF was added. The mixture was stirred for about 4 hours at room temperature. This mixture is diluted with ethyl acetate and thoroughly washed with water. The ethyl acetate portion is dried over sodium sulfate, filtered and evaporated to give the title compound.

In like manner and using sufficient quantities of chloromethyl acetate, chloromethyl propionate, and chloromethyl butyrate in place of chloromethyl pivalate, the following respective products are prepared:

3-[(Acetyloxy)methyl]-7-[[2-carboethoxy-2-(1-pyrryl)-acetyl]amino]-8-oxo-5-thia-1-azabicyclo[4.2.0]oct-2-ene-2-carboxylic acid acetyloxymethyl ester, 3-[(Acetyloxy)methyl]-7-[[2-carboethoxy-2-(1-pyrryl)-acetyl]amino]-8-oxo-5-thia-1-azabicyclo[4.2.0]oct-2-ene-2-carboxylic acid propionyloxymethyl ester, and 3-[(Acetyloxy)methyl]-7-[[2-carboethoxy-2-(1-pyrryl)-acetyl]amino]-8-oxo-5-thia-1-azabicyclo[4.2.0]oct-2-ene-2-carboxylic acid butyryloxymethyl ester.

EXAMPLE 19

7-[[2-(3-Carboethoxypropyl)-2-(1-pyrryl)acetyl]amino]-7-methoxy-3-[[(1-methyltetrazol-5-yl)thio]methyl]-8-oxo-5-thia-1-azabicyclo[4.2.0]oct-2-ene-2-carboxylic acid p-pivaloyloxybenzyl ester 7-[[2-(3-Carboethoxypropyl)-2-(1-pyrryl)acetyl]amino]-7-methoxy-3-[[(1-methyltetrazol-5-yl)thio]methyl]-8-oxo-5-thia-1-azabicyclo[4.2.0]oct-2-ene-2-carboxylic acid, sodium salt, 6.6 mmole, is added to 35 ml of dimethylformamide (DMF) with stirring. Then 2 equivalents of pivaloyloxybenzyl alcohol is added and the mixture cooled to 0° C. To this is added 7.2 mmole of dicyclohexylcarbodiimide in 7.5 ml of DMF. Stirring is continued at 0° C. for 1 hour and an additional 4 hours at room temperature. The dicyclohexyl urea which is formed is removed by filtration. The reaction mix is diluted with ethyl acetate, washed thoroughly with water and the ethyl acetate is dried and filtered. Evaporation of the ethyl acetate gives the title compound.

In like manner substituting sufficient quantities of p-acetyloxybenzyl alcohol, p-propionyloxybenzyl alcohol and p-valeryloxybenzyl alcohol for p-pivaloyloxybenzyl alcohol, the respective compounds are produced:

7-[[2-(3-carboethoxypropyl)-2-(1-pyrryl)acetyl]amino]-7-methoxy-3-[[(1-methyltetrazol-5-yl)thio]methyl]-8-oxo-5-thia-1-azabicyclo[4.2.0]oct-2-ene-2-carboxylic acid p-acetyloxybenzyl ester, 7-[[2-(3-carboethoxypropyl)-2-(1-pyrryl)acetyl]amino]-7-methoxy-3-[[(1-methyltetrazol-5-yl)thio]methyl]-8-oxo-5-thia-1-azabicyclo[4.2.0]oct-2-ene-2-carboxylic acid p-propionyloxybenzyl ester, and 7-[[2-(3-carboethoxypropyl)-2-(1-pyrryl)acetyl]amino]-7-methoxy-3-[[(1-methyltetrazol-5-yl)thio]methyl]-8-oxo-5-thia-2-azabicyclo[4.2.0]oct-2-ene-carboxylic acid p-valeryloxybenzyl ester.

EXAMPLE 20

3-[(Acetyloxy)methyl]-7-[[2-carboethoxy-2-(1-pyrryl)-acetyl]amino]-8-oxo-5-thia-1-azabicyclo[4.2.0]oct-2-ene-2-carboxylic acid N-ethoxy-N-methyl aminomethyl ester The sodium salt of 3-[(acetyloxy)methyl]-7-[[2-carboethoxy-2-(1-pyrryl)acetyl]amino]-8-oxo-5-thia-1-azabicyclo[4.2.0]oct-2-ene-2-carboxylic acid, 2.5 mmole, in 50 ml of dimethylformamide (DMF) is treated at room temperature with 2.5 mmole of N-chloromethyl-N-methylurethane for 1 hour. The mixture is carefully poured into ice water and the precipitated solid is removed by filtration and washed with water. The solid is dissolved in ethyl acetate and washed with aqueous sodium bicarbonate and then with water. The ethyl acetate is dried, filtered and evaporated to give the title compound.

In like manner and substituting the appropriate quantities of N-methyl-N-propionylaminomethyl chloride, or N-acetylaminomethyl chloride for the N-chloromethylurethane the following respective compounds are obtained:

3-[(Acetyloxy)methyl]-7-[[2-carboethoxy-2-(1-pyrryl)-acetyl]amino]-8-oxo-5-thia-1-azabicyclo[4.2.0]oct-2-ene-2-carboxylic acid N-methyl-N-propionylaminomethyl ester, and 3-[(Acetyloxy)methyl]-7-[[2-carboethoxy-2-(1-pyrryl)-acetyl]amino]-8-oxo-5-thia-1-azabicyclo[4.2.0]oct-2-ene-2-carboxylic acid N-acetylaminomethyl ester.

EXAMPLE 21

7-[[2-Carboethoxy-2-(1-pyrryl)acetyl]amino]-7-methoxy-3-methyl-8-oxo-5-thia-1-azabicyclo[4.2.0]oct-2-ene-2-carboxylic acid 2-(1-Pyrryl)propanedioic acid, 3-ethyl ester, 1 equivalent and 1 equivalent of triethylamine is added to tetrahydrofuran (THF) which is cooled to 0° C. While stirring, iso-butyl chloroformate, 1 equivalent, is added and the temperature is maintained at 0° C. for about 15 minutes. A cold solution of 7-amino-7-methoxy-3-methyl-8-oxo-5-thia-1-azabicyclo[4.2.0]oct-2-ene-2-carboxylic acid, 1 equivalent, and triethylamine, 1 equivalent, in 50% aqueous THF is added with stirring to the previous solution.

The mixture is stirred at 5° for 1 hour and at room temperature for an additional hour. The tetrahydrofuran is evaporated and the residue is dissolved in water and is washed with ethyl acetate. The aqueous phase is covered with a fresh layer of ethyl acetate, cooled in ice and acidified to pH of 3 with 6N hydrochloric acid. The mixture is filtered and the ethyl acetate separated. The aqueous phase is washed with fresh ethyl acetate. The combined ethyl acetate washings are dried over magnesium sulfate, treated with charcoal, filtered and concentrated. The concentrate is added to a stirred mixture of etherhexane which precipitates the title compound which is recovered by filtration.

The daily dosage of the active ingredient may range from 1 mg to about 500 mg. The exact amount will vary with the patients size, age and type of infection.

A typical tablet can have the following composition

| | |
|---|---|
| 3-[(Acetyloxy)methyl]-7-[[2-carboethoxy-2-(1-pyrryl)acetyl]amino]-8-oxo-5-thia-1-azabicyclo[4.2.0]-oct-2-ene-2-carboxylic acid. | 50 mg |
| Lactose, USP | 250 mg |
| Corn Starch, USP | 50 mg |
| Corn Starch, USP (as 10% starch paste) | 5 mg |
| Calcium Stearate | 2 mg |

Suitable size tablets can be prepared using a 5/16 inch diameter standard concave punch.

A typical ointment can have the following composition

3-[(Acetyloxy)methyl]-7-[[2-carboethoxy-2-(1-pyrryl)-acetyl]amino]-8-oxo-5-thia-1-azabicyclo[4.2.0]oct-2-ene-2-carboxylic acid.

| Hydrophilic Base | |
|---|---|
| Cetyl alcohol | 15% |
| White Wax | 1% |
| Sodium Lauryl sulfate | 2% |
| Propylene glycol | 10% |
| Water | 72% |

Add the cephalosporin derivative to a small amount of water and incorporate into the base.

A typical parenteral solution may have the following composition:

| | |
|---|---|
| 3-[(Acetyloxy)methyl]-7-[[2-carboethoxy-2-(1-pyrryl)acetyl]amino]-8-oxo-5-thia-1-azabicyclo[4.2.0]oct-2-ene-2-carboxylic acid | 1.0 g |
| White beeswax | 1.0 g |
| Peanut oil, to make | 10.0 cc |

Melt wax into a portion of the peanut oil and then add the remaining oil to the mix. Sterilize the mix at 150° C. for 2 hours with dry heat. Under sterile conditions mix the cephalosporin into the wax-oil mixture and place in an ampule and seal said ampule. For use, dilute contents of ampule with 10 cc of pure water. Each cc contains 50 mg of cephalosporin.

We claim:

1. A compound selected from the base of the formula

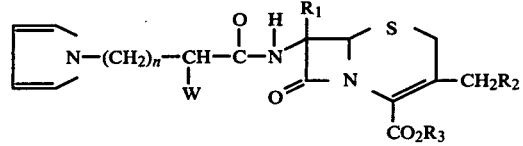

wherein n is 0, 1, 2 or 3; W is hydrogen, a straight or branched alkyl group of from 1 to 5 carbon atoms; a sulfonic acid group, or a $-(CH_2)_z-CO_2R_4$ group wherein Z is 0 or an integer from 1 to 10 and $R_4$ is hydrogen, non-toxic pharmaceutically acceptable cation selected from the alkali metal or alkaline earth metal groups, ammonium and an organic ammonium group, a straight or branched 1 to 4 carbon alkyl group, a straight or branched alkanoyloxymethyl group in which the alkanoyl moiety has from 2 to 5 carbon atoms; $R_1$ is hydrogen or methoxy; $R_2$ is 1,3,4-thiadiazol-2-ylthio; 5-methyl-1,3,4-thiadiazol-2-ylthio; tetrazol-5-ylthio; 1-methyltetrazol-5-ylthio; 1,3,4-oxadiozol-2-ylthio; 5-methyl-1,3,4-oxadiozol-2-ylthio; 1-methyl-1,2,3-triazol-5-ylthio; 1,2,3-triazol-5-ylthio; $R_3$ is hydrogen, a non-toxic pharmaceutically acceptable cation of an alkali metal or an alkaline earth metal, ammonium or an organic ammonium group, a straight or branched alkyl group of from 1 to 4 carbon atoms, a straight or branched alkanoyloxymethyl group in which the alkanoyl moiety has from 2 to 5 carbon atoms and is straight or branched, an alkanoylaminomethyl group in which the alkanoyl moiety is straight or branched and has from 2 to 5 carbon atoms and the amine nitrogen may be substituted with a straight or branched alkyl group having 1 to 4 carbon atoms; an alkoxycarbonylaminomethyl group in which the alkoxy moiety is straight or branched and has from 1 to 4 carbon atoms and the amine nitrogen may be substituted with a straight or branched alkyl group of from 1 to 4 carbon atoms, p-(alkanoyloxy)benzyl group in which the alkanoyl moiety is straight or branched and has from 2 to 5 carbon atoms; an aminoalkanoyloxymethyl group in which the alkanoyl moiety has from 2 to 15 carbon atoms and the amino nitrogen may be mono- or di-substituted with a straight or branched alkyl group having from 1 to 4 carbon atoms; with the proviso that when n is 0, W must be an alkyl group, a sulfonic acid group of a $-(CH_2)_z-CO_2R_4$ group with $R_4$ as defined above; and with the further proviso that when $R_3$ is other than hydrogen or a cation and W is $-(CH_2)_z-CO_2R_4$ with z being from 1 to 10 then $R_4$ is other than hydrogen or a cation, and pharmaceutically acceptable salts thereof.

2. A compound according to claim 1 wherein $R_1$ is hydrogen.

3. A compound according to claim 1 wherein $R_1$ is methoxy.

4. A compound according to claim 2 wherein $R_3$ is hydrogen.

5. A compound according to claim 4 wherein W is a carbethoxy group.

6. A compound according to claim 4 wherein $R_2$ is
   1,3,4-thiadiazol-2-ylthio; 5-methyl-1,3,4-thiadiazol-2-ylthio; tetrazol-5-ylthio; 1-methyltetrazol-5-ylthio;
   1,3,4-oxadiazol-2-ylthio; 5-methyl-1,3,4-oxadiazol-2-ylthio; 1-methyl-1,2,3-triazol-5-ylthio; and 1,2,3-triazol-5-ylthio or a pharmaceutically acceptable salt thereof.

7. A compound selected from the base of the formula

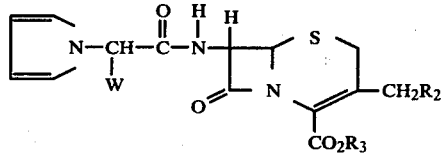

wherein W is a straight or branched alkyl group of from 1 to 5 carbon atoms; a sulfonic acid group, or a $-(CH_2)_z-CO_2R_4$ group wherein Z is 0 or an integer from 1 to 10 and $R_4$ is hydrogen, a cation selected from the alkali metal or alkaline earth metal groups, ammonium and organic ammonium cations, a straight or branched 1 to 4 carbon alkyl group, a straight or branched alkanoyloxymethyl group in which the alkanoyl moiety has from 2 to 5 carbon atoms; $R_2$ is 1,3,4-thiadiazol-2-ylthio; 5-methyl-1,3,4-thiadiazol-2-ylthio; tetrazol-5-ylthio; 1-methyltetrazol-5-ylthio; 1,3,4-oxadiazol-2-ylthio; 5-methyl-1,3,4-oxadiazol-2-ylthio; 1-methyl-1,2,3-triazol-5-ylthio; $R_3$ is hydrogen, a cation of an alkali metal or an alkaline earth metal, ammonium or organic ammonium cations, a straight or branched alkyl group of from 1 to 4 carbon atoms, an alkanoyloxymethyl group in which the alkanoyl moiety has from 2 to 5 carbon atoms and is straight or branched, an alkanoylaminomethyl group in which the alkanoyl moiety is straight or branched and has from 2 to 5 carbon atoms and the amine nitrogen may be substituted with a straight or branched alkyl group having 1 to 4 carbon atoms; an alkoxycarbonylaminomethyl group in which the alkoxy moiety is straight or branched and has from 1 to 4 carbon atoms and the amine nitrogen may be substituted with a straight or branched alkyl group of from 1 to 4 carbon atoms, p-(alkanoyloxy)benzyl group in which the alkanoyl moiety has from 2 to 15 carbon atoms and the amino nitrogen may be mono- or di-substituted with a straight or branched alkyl group having from 1 to 4 carbon atoms, with the proviso that when $R_3$ is other than H when W is $-(CH_2)_{1-10}-CO_2R_4$ then $R_4$ is also other than H, and pharmaceutically acceptable salts thereof.

8. A compound according to claim 7 wherein $R_3$ is hydrogen.

9. A compound according to claim 8 wherein $R_2$ is 1,3,4-thiadiazol-2-ylthio; 5-methyl-1,3,4-oxadiazol-2-ylthio; 1-methyl-1,2,3-triazol-5-ylthio or 1,2,3-triazol-5-ylthio or a pharmaceutically acceptable salt thereof.

10. A compound according to claim 9 which is 7-[[2-carboethoxy-2-(1-pyrryl)acetyl]amino]-7-[[(1,3,4-thiadiazol-2-yl)thio]methyl]-8-oxo-5-thia-1-azabicyclo[4.2.0]oct-2-ene-2-carboxylic acid or a pharmaceutically acceptable salt thereof.

11. A compound according to claim 9 which is 7-[[2-carboethoxy-2-(1-pyrryl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid or a pharmaceutically acceptable salt thereof.

12. A compound according to claim 9 which is 7-[[2-carboxy-2-(1-pyrryl)acetyl]amino]-3-[[(1,3,4-thiadiazol-2-yl)thio]methyl]-8-oxo-5-thia-1-azabicyclo[4.2.0]oct-2-ene-2-carboxylic acid or a pharmaceutically acceptable salt thereof.

13. A compound according to claim 9 which is 7-[[2-carboxy-2-(1-pyrryl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid or a pharmaceutically acceptable salt thereof.

14. A compound according to claim 9 which is 7-[[2-carboethoxy-2-(1-pyrryl)acetyl]amino]-3-[[(tetrazol-5-yl)thio]methyl]-8-oxo-5-thia-1-azabicyclo[4.2.0]-oct-2-ene-2-carboxylic acid or a pharmaceutically acceptable salt thereof.

15. A compound according to claim 9 which is 7-[[2-carboethoxy-2-(1-pyrryl)acetyl]amino]-3-[[(1-methyltetrazol-5-yl)thio]methyl]-8-oxo-5-thia-1-azabicyclo[4.2.0]oct-2-ene-2-carboxylic acid or a pharmaceutically acceptable salt thereof.

16. A compound according to claim 9 which is 7-[[2-carboxy-2-(1-pyrryl)acetyl]amino]-3-[[(tetrazol-5-yl)thio]methyl]-8-oxo-5-thia-1-azabicyclo[4.2.0]oct-2-ene-2-carboxylic acid or a pharmaceutically acceptable salt thereof.

17. A compound according to claim 9 which is 7-[[2-carboxy-2-(1-pyrryl)acetyl]amino]-3-[[(1-methyltetrazol-5-yl)thio]methyl]-8-oxo-5-thia-1-azabicyclo[4.2.0]oct-2-ene-2-carboxylic acid or a pharmaceutically acceptable salt thereof.

* * * * *